US008513476B2

(12) United States Patent
Gomes et al.

(10) Patent No.: US 8,513,476 B2
(45) Date of Patent: Aug. 20, 2013

(54) PROCESS FOR PRODUCING LIGHT OLEFINS FROM A FEED CONTAINING TRIGLYCERIDES

(75) Inventors: Jefferson Roberto Gomes, Rio de Janeiro (BR); Júlio Amílcar Ramos Cabral, Rio de Janeiro (BR); Andrea de Rezende Pinho, Rio de Janeiro (BR); Luis Fernando Soares de Azevedo, Rio de Janeiro (BR)

(73) Assignee: Petroleo Brasileiro S.A.-Petrobras, Rio de Janeiro (BR)

( * ) Notice: Subject to any disclaimer, the term of this patent is extended or adjusted under 35 U.S.C. 154(b) by 726 days.

(21) Appl. No.: 12/477,352

(22) Filed: Jun. 3, 2009

(65) Prior Publication Data

US 2009/0326293 A1 Dec. 31, 2009

(30) Foreign Application Priority Data

Jun. 3, 2008 (BR) ...................................... 0802222

(51) Int. Cl.
*C07C 4/06* (2006.01)

(52) U.S. Cl.
USPC ........................................................ 585/324

(58) Field of Classification Search
USPC ........................................................ 585/324
See application file for complete search history.

(56) References Cited

U.S. PATENT DOCUMENTS

| 5,504,259 A | 4/1996 | Diebold et al. | |
| 5,951,963 A * | 9/1999 | He et al. | 423/713 |
| 7,288,685 B2 * | 10/2007 | Marker | 585/240 |
| 2006/0186020 A1 | 8/2006 | Gomes | |
| 2009/0004715 A1 * | 1/2009 | Trimbur et al. | 435/166 |

FOREIGN PATENT DOCUMENTS

| BR | PI 8304794 | 9/1983 |
| BR | PI 0500591-4 | 2/2005 |

* cited by examiner

*Primary Examiner* — Thuan D Dang
(74) *Attorney, Agent, or Firm* — Sughrue Mion, PLLC

(57) ABSTRACT

The process combines hydroconversion and catalytic cracking starting from a feed containing triglycerides, at concentrations of fatty acids above 85%, which maximizes the yields of light olefins, chiefly ethylene and propylene, while reducing the yield of gasoline, with conversion greater than 80 wt. %.

18 Claims, 1 Drawing Sheet

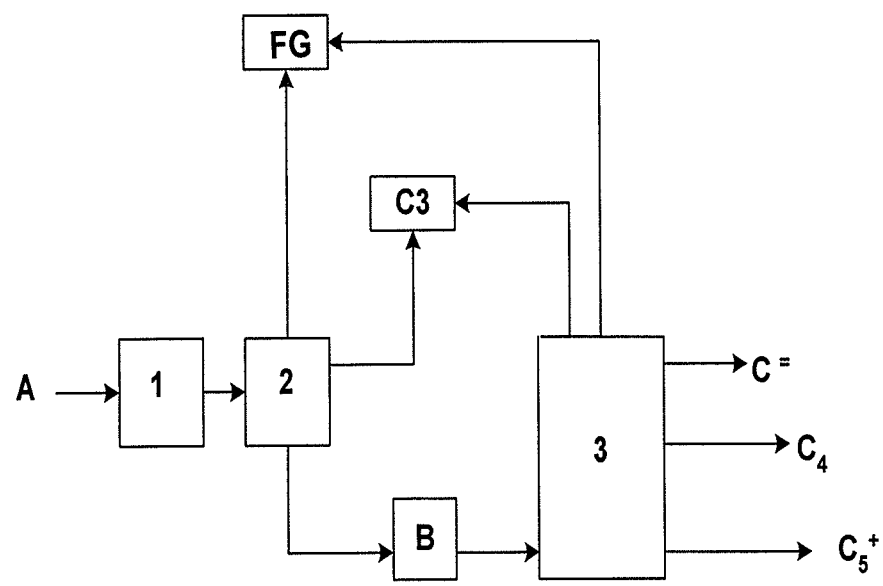

PROCESS FOR PRODUCING LIGHT OLEFINS FROM A FEED CONTAINING TRIGLYCERIDES

FIELD OF THE INVENTION

The process relates to the production of light olefins from feeds containing triglycerides, obtained from vegetable and/or animal biomass. More specifically, the process combines the catalytic hydroconversion of the triglycerides, to obtain a liquid fraction of linear paraffinic hydrocarbons, and the catalytic cracking of this liquid fraction in process conditions for maximizing the production of ethylene and propylene.

BACKGROUND OF THE INVENTION

There is now considerable interest in the processing of vegetable and/or animal biomass to obtain fuels such as biodiesel and ethanol, in place of non-renewable fossil fuels, and thus contribute to improvement of the conditions of the environment.

Starting from vegetable and/or animal biomass, triglyceride-rich organic oils are usually obtained, and are widely used in industry.

The hydroconversion of these triglyceride-rich organic oils, mixed with diesel oil from petroleum, is an advantageous alternative that adds quality to the fuel produced, as described in patent document PI 0500591-4 for a process for conversion to paraffinic hydrocarbons with boiling point in the diesel oil range.

In general, a process of hydroconversion of organic oils, obtained from vegetable and/or animal biomass, comprises the reaction of hydrogen with the fatty acids making up the molecules of the triglycerides to produce paraffinic hydrocarbons.

The process of hydroconversion, designated HDT, includes the passage of a hydrocarbon stream, in contact with a hydrogen stream, in a fixed catalyst bed, under conditions of pressure between 1 MPa and 15 MPa, and temperature between 280° C. and 400° C. Commercial catalysts are usually employed in the form of metal oxide (Ni and Mo, Co and Mo, Ni and W), supported on gamma alumina, said catalysts being sulphided to obtain the most active form of the catalyst bed in the process.

An important factor in the conventional HDT process, making it difficult to use organic oil feeds obtained from biomass, is the highly exothermic character of the reactions of hydroconversion of the triglycerides of the feed in a reactor that operates adiabatically with increasing temperature along the catalyst bed. However, to minimize the undesirable effects of excessive temperature along the catalyst bed, an HDT reactor can be designed with more than one catalyst bed, with injection of a recycle stream between the beds, to reduce the rate of temperature rise in the catalyst bed of the reactor.

To summarize, a process of HDT of feed containing triglycerides is based on the molecular structure of the constituents of the feed and on the characteristics of the catalyst employed in the process. In conditions of hydroconversion, initially there are reactions of hydrogenation of the double bonds, followed by reactions of thermal cracking of the saturated molecules of higher molecular weight. The size of the saturated molecules promotes the reactions of thermal cracking, in conditions of high temperatures, forming carboxylic acids and acrolein. For example, in the conversion of soya oil, the carboxylic acids may undergo thermal degradation by reactions of decarboxylation resulting in nC17 and $CO_2$, as well as reactions of decarbonylation with the production of nC17, CO and water; and reactions of dehydration producing nC18 and water. It is also thought that a molecule of acrolein reacts in the presence of the catalyst and hydrogen producing propane, and the CO also reacts, producing methane and water.

Also applied for production of fuels, the processes of catalytic cracking of organic oils obtained from vegetable and/or animal biomass represent an alternative to the processing of petroleum distillates, and are also applied for the production of light and aromatic olefins, which are of considerable economic value for the petrochemical industry.

Usually, in petrochemical fluid catalytic cracking—FCC, feeds are processed with boiling points from the range of naphthas up to that of atmospheric residues, with the aim of producing hydrocarbons of even smaller molecular size than those found in a gasoline, in particular molecules of the olefins ethylene and propylene ($C_2^=$ and $C_3^=$). Usually, these products are maximized by increasing the conversion, with a decrease in the production of heavy products such as decanted oil (DO) and light cycle oil (LCO), as well as through selectivity, minimizing the formation of undesirable by-products such as coke and fuel gas.

To achieve this aim, the catalytic system is modified, normally by adding, to a typical catalyst, a special component that is able to convert olefins with five to eight carbon atoms to smaller olefins.

Optionally, an increase in reaction temperature is required, to a value that may exceed 620° C. at reactor outlet (TRX). However, high reaction temperatures impair the selectivity of the reactions of catalytic cracking, producing an undesirable increase in yield of fuel gas. High temperatures also promote the formation of aromatic hydrocarbons with boiling points in the range of gasoline and of LCO, which are poorly reactive products in catalytic cracking and interrupt the sequence of reactions that would produce desirable light products. Another negative aspect of high temperature is the production of butadienes, coke precursors which may be deposited in the transfer line and in the reactor vessel.

Besides the reaction temperature and the specificity of the catalyst, another important aspect for the reactions of cracking in a petrochemical FCC process is the initial contact of the catalyst with the feed, which has a decisive influence on the conversion and the selectivity of the process for generating higher-value products. Therefore it is important to have the maximum possible atomization of the feed in the injectors, in order to guarantee the homogeneity of the catalyst/feed mixture, at the inlet of the FCC reactor.

For production of olefins in the petrochemical FCC, catalysts can be used that contain zeolites of type Y, supported on an active matrix of alumina and a binder, said zeolites preferably having a low content of rare earths in their composition. It is also possible to use zeolites of type ZSM-5¹, a special component capable of converting olefins with five to eight carbon atoms to smaller olefins.

The catalysts used for petrochemical cracking should contain zeolites of type USY, REY and ZSM, the zeolites of type ZSM with silica-alumina ratio equal to 10 or more, including for example zeolites ZSM-5 (MFI), ZSM-11, ZSM-12 and ZSM-35, being the main ones used for the conversion of hydrocarbons.

In the petrochemical FCC of vegetable oils, we may mention in particular patent PI 8304794, which teaches the process conditions for obtaining greater conversion of a feed of soya oil, compared with the results for FCC of a usual feed of gas oil.

U.S. Pat. No. 7,288,685 teaches a petrochemical FCC process for the production of olefins from a feed of vegetable oils, previously purified of metallic contaminants, using a zeolitic catalyst, containing zeolites of type ZSM as principal constituent. In general, the results from a petrochemical FCC process show an increase in the production of olefins accompanying the increase in severity of the process, but there is also increased formation of fuel gas and coke, as well as other hydrocarbons heavier than the constituents with boiling point in the naphtha range.

Moreover, petrochemical FCC can be applied in combined processing of biomass, as taught in U.S. Pat. No. 5,504,259 for the production of gasoline from biomass and plastic waste such as PVC and polyethylene. In this case, the feed first undergoes a pyrolysis stage and the oily liquid product from pyrolysis is then submitted to catalytic cracking, to generate light olefins that are oligomerized with alcohol for the production of ether, which can be added to gasoline to increase the overall yield of the product.

Therefore there is clearly a search for alternatives for the processing of biomass to obtain products of higher economic value, such as light olefins ($C_2^=$ and $C_3^=$) and gasoline (C5+).

In the following, a process is described that combines hydroconversion and catalytic cracking so as to obtain gains in conversion and selectivity for the production of light olefins ($C_2^=$ and $C_3^=$), from a feed containing triglycerides of vegetable and/or animal biomass, with a high degree of conversion of the process.

SUMMARY OF THE INVENTION

Broadly speaking, the process for production of light olefins, with maximization of ethylene and propylene, combines a hydroconversion stage—HDT of a feed containing triglycerides for obtaining a liquid fraction of paraffinic hydrocarbons and a stage of fluid catalytic cracking—FCC in conditions of petrochemical cracking.

The products of the hydroconversion are separated into three fractions, namely:

a) a fraction of fuel gas and water vapour;
b) a gaseous fraction constituted mainly of propane; and
c) a liquid fraction of saturated hydrocarbons (C9-C18) and dissolved gases.

After separation, the liquid fraction of saturated hydrocarbons is submitted directly to a stage of cracking on a zeolite-rich catalyst, preferably of type ZSM-5, in proportions between 1 and 55 wt. %.

In this way, the process provides greater selectivity for light olefins, chiefly ethylene and propylene ($C_2^=$ and $C_3^=$), as well as a higher degree of conversion when compared with the cracking of a hydrogenated diesel oil or compared with FCC of organic oil containing triglycerides, without the hydroconversion stage. The gains in selectivity and degree of conversion, greater than 80 wt. %, are illustrated in the examples.

BRIEF DESCRIPTION OF THE DRAWINGS

The appended FIG. 1 shows the process flowsheet with the stages of: hydroconversion—HDT (1), separation (2) of the liquid fraction (B) and fluid catalytic cracking—FCC (3) of the liquid fraction, from a triglyceride-rich feed (A) obtained from vegetable and/or animal biomass for maximizing the production of light olefins ($C^=$), chiefly ethylene and propylene. Other products are: fuel gas (FG), propane (C3), butane and butenes (C4) and gasoline ($C_5^+$).

DETAILED DESCRIPTION OF THE INVENTION

The aim of the process described below is to produce light olefins ($C_2^=$ and $C_3^=$), from a feed containing triglycerides with fatty acids of (C9-C18) carbon chain obtained from vegetable and/or animal biomass.

Said triglycerides and/or fatty acids are present at high concentration in: soya oil (*Glycine max*), castor oil (*Ricinus communis*), cottonseed oil (*Gossypium hirsutum* or *G. barbadenseis*), oil of Brazilian oil palm (*Elaies guinensis*), pine oil (tall oil), sunflower oil (*Helianthus annuus*), oil of Barbados nut or Physic nut (*Jatropha curcas*), seaweed oil, tallow, and other oils of animal or vegetable origin.

For the process, the feed can include a single oil or a mixture of two or more oils, in any proportions, without limiting the use of other raw materials, containing concentrations above 65 wt. % of triglycerides and/or fatty acids.

Feeds of organic oils, predominantly paraffinic (for example: oil of Brazilian oil palm and oil of animal origin) are the most suitable as they consume less hydrogen in the hydroconversion stage. Prior removal of inorganic contaminants such as: Na, K, Ca and P, which poison the HDT catalyst, is also recommended.

In the process, a feed is fed into the reactor of hydroconversion—HDT, preferably diluted with a recycle stream of hydrocarbons formed in the hydroconversion, to reduce the rate of temperature rise in the catalyst bed of the reactor. The hydroconversion removes the oxygen atoms and the unsaturations from the molecules of the triglycerides, obtaining:

a) a fraction of fuel gas and water vapour;
b) a gaseous fraction constituted principally of propane; and
c) a liquid fraction of saturated hydrocarbons (C9-C18) and dissolved gases.

The liquid fraction is separated and is fed, vaporized, into the fluidized-bed catalytic cracking reactor—FCC, in contact with zeolite-rich catalyst of type ZSM, preferably ZSM-5, in conditions of petrochemical cracking for maximizing the production of light olefins, chiefly ethylene and propylene ($C_2^=$ and $C_3^=$), with a degree of conversion above 80 wt. %.

The process is described below according to the flowsheet in FIG. 1, and the results are presented in the examples.

A feed containing triglycerides is hydrogenated in a hydroconversion stage (1), in contact with a hydrogen-rich gas stream, under conditions of temperature between 280° C. and 370° C., hydrogen partial pressure between 2 MPa and 10 MPa and space velocity LHSV between 0.5 and 2.5 $h^{-1}$, depending on the structure of the molecules of the triglycerides in the feed, in a catalyst bed of metal oxides (Ni and Mo, Co and Mo, Ni and W), sulphided, supported on gamma alumina, MgO or silica/alumina.

In this stage the triglycerides and/or fatty acids are completely hydrogenated, and the yield of the liquid fraction of saturated hydrocarbons (C9-C18), free from oxygen, is greater than 80 wt. %, as shown in Table 1, which presents the typical data for yield of products from the reactions of hydroconversion of a refined soya oil, containing predominantly C17-C18 fatty acids.

TABLE 1

| Products | wt. % |
|---|---|
| CO | 1.3 |
| $CO_2$ | 4.6 |
| Methane | 0.3 |
| Propane | 5.0 |
| $H_2O$ | 7.7 |
| Liquid fraction | 82.4 |

Table 2 presents data for the typical composition of the liquid fraction of hydrocarbons obtained in the hydroconversion stage of a refined soya oil.

TABLE 2

| Products | % w/w |
|---|---|
| nC15 | 4.2 |
| nC16 | 6.7 |
| nC17 | 32.8 |
| nC18 | 48.6 |

After the hydroconversion stage, the resultant effluent goes to a separation stage (2) to obtain the fractions:
a) a fraction of fuel gas (FG), containing $C_1$-$C_2$ hydrocarbons;
b) a gaseous fraction (C3) constituted predominantly of propane; and
c) a liquid fraction (B), constituted predominantly of saturated hydrocarbons with a linear carbon chain (C9-C18) depending on the structure of the triglycerides in the feed.

Next, the liquid fraction is sent directly to a stage of fluid catalytic cracking—FCC (3), in conditions for maximizing the production of light olefins, chiefly $C_2^=$ and $C_3^=$, presenting a profile of yield of products that corresponds to the competing reactions of catalytic cracking and thermal cracking, depending on the process conditions.

Usually, with the aim of maximizing the production of light olefins, operating conditions are applied that are extremely severe for a petrochemical FCC of feeds constituted of hydrocarbons from petroleum refining.

For the present process, in the FCC reactor, the liquid fraction of paraffinic hydrocarbons is vaporized and comes in contact with a catalyst with a high content of zeolites, preferably between 30 and 70 wt. %, at temperatures above 700° C., admitting, at the bottom of the reactor, an amount of steam between 5 and 50 wt. % relative to the feed entering the reactor. The residence time varies between 1 and 10 seconds inside the reactor and the temperature at reactor outlet TRX can vary from 450° C. to 620° C. Dense-phase reactors can also be used, with residence times between 10 and 60 seconds.

At reactor outlet, the products of the cracking reactions are separated from the catalyst, which is then regenerated to restore the catalytic activity and recycled to the reactor.

To increase the yield of light olefins, in the FCC reactor the LCO produced can be recycled to the process.

A zeolite ZSM-5 with average pore size between 5 Å and 7 Å in diameter is preferably used, in proportions between 1% and 55 wt. % relative to the catalyst, and it is also possible for other zeolites with high silica-alumina ratio, such as ZSM-8, ZSM-11, ZSM-12 or ZSM-35, to be used in the same proportions.

These zeolites are usually combined with an inert binder, making up less than 20 wt. % of the final composition of the catalyst, it being recommended to use a catalyst with a particle diameter between 20 and 200 μm.

Other metals can be incorporated in the structure of the zeolite to improve its properties, increasing or stabilizing its activity. For example, the element phosphorus can be incorporated in zeolite ZSM-5, separately, or in the catalyst with the zeolite, by means of a solution containing the element, the catalyst particles then being dried and calcined.

A special catalyst can be incorporated in the catalyst for the specific purpose of converting larger olefins, with boiling points typical of a gasoline ($C_5^+$), into smaller olefins, shifting the selectivity of the FCC towards increase in yield of light olefins while reducing the yield of ($C_5^+$) gasoline.

The results of the gains in selectivity and conversion of the process, combining a hydroconversion stage with a stage of catalytic cracking, can be confirmed by the following examples, which do not, however, limit the scope of the invention. There are clear gains in selectivity for light olefins, chiefly $C_2^=$ and $C_3^=$, for the process as compared with FCC of a feed of refined soya oil or with FCC of another feed of diesel oil from petroleum refining. It can also be seen that the degree of conversion is greater than 80 wt. %.

In addition to light olefins, the process generates sulphur-free gasoline, propane and butane, which can then be submitted to a pyrolysis stage to produce more ethylene.

Therefore the process of the present invention, combining hydroconversion and catalytic cracking, provides maximization of the production of light olefins, chiefly ethylene and propylene, from a feed containing triglycerides and/or fatty acids obtained from vegetable and/or animal biomass.

EXAMPLES

Two series of tests were carried out in a pilot-plant unit, in particular with a feed of refined soya oil, according to the process stages for production of light olefins, to demonstrate the characteristics of the process, including the stages of:
a) hydroconversion of a feed constituted of refined soya oil fed to the HDT reactor, in liquid phase, diluted with 80 wt. % of a recycle stream of saturated hydrocarbons, in contact with a hydrogen stream on a sulphided catalyst bed of NiMo supported on gamma alumina, under conditions of 3.5 MPa of pressure, 320° C. of WABT (weighted average temperature) and LHSV of 1.5 h$^{-1}$;
b) separation of the products from the hydroconversion reactions into 3 fractions, obtaining a liquid fraction of saturated hydrocarbons, predominantly C17-C18, part of this fraction constituting the recycle stream for the HDT reactor; and
c) catalytic cracking of the liquid fraction vaporized and fed to the FCC reactor, in a catalyst bed containing from 1 to 55 wt. % of ZSM-5 to maximize the yield of light olefins, chiefly ethylene and propylene ($C_2^=$ and $C_3^=$), while reducing the yield of gasoline (C5+).

The results for the yields of products formed in the hydroconversion stage are presented in Table 3, showing higher concentration of (C17-C18) in the liquid fraction that is to be sent to the catalytic cracking stage of the process.

TABLE 3

| Products | wt. % |
|---|---|
| CO | 1.3 |
| CO$_2$ | 4.5 |
| C1 | 0.3 |
| C3 | 4.9 |
| H$_2$O | 7.6 |
| C15 | 3.6 |
| C16 | 6.0 |
| C17 | 28.0 |
| C18 | 43.7 |

The next Table 4 presents a summary of the results of tests A-E with yields of products obtained for each set of conditions of temperature (TRX) at the top of the reactor, between 520° C. and 620° C., in the stage of petrochemical FCC, with the liquid fraction of saturated hydrocarbons (C15-C18) formed in the hydroconversion stage.

TABLE 4

| Yield, wt. % | TRX, ° C. | | | | |
|---|---|---|---|---|---|
| | 520 A | 550 B | 580 C | 600 D | 620 E |
| Fuel Gas | 1.5 | 2.2 | 3.1 | 4.0 | 5.2 |
| $C_2^=$ | 6.6 | 9.5 | 11.9 | 14.5 | 16.5 |
| $C_3$ | 6.0 | 6.7 | 6.8 | 7.7 | 7.6 |
| $C_3^=$ | 22.3 | 25.7 | 27.6 | 27.7 | 28.5 |
| $C_4$ | 6.4 | 6.6 | 6.3 | 6.2 | 5.5 |
| $C_4^=$ | 18.3 | 17.1 | 16.7 | 14.6 | 12.8 |
| $C_5$ –221° C. | 29.3 | 26.7 | 23.1 | 22.0 | 19.9 |
| LCO, 221-343° C. | 8.2 | 4.2 | 2.8 | 1.8 | 1.6 |
| DO, +343° C. | 0.3 | 0.1 | 0.1 | 0.0 | 0.1 |
| Coke | 1.0 | 1.1 | 1.4 | 1.3 | 2.1 |
| Conversion | 90.5 | 94.6 | 95.7 | 96.9 | 96.2 |

As shown in Table 4, there are gains in conversion in the process, and greater selectivity for the production of ($C_2^=$ and $C_3^=$) with increase of the temperature in the FCC stage, while reducing the production of gasoline ($C_5$+) and of C4, also minimizing the production of undesirable products such as light cycle gas oil (LCO), decanted oil (DO) and coke. Conversely, we also observe an increase in thermal cracking as the temperature rises, demonstrated by the increase in yield of fuel gas and coke, which are still extremely low yields compared with those of the FCC process of a hydrofined diesel oil or of a refined soya oil, as confirmed below, by the data in Tables 6 and 7.

In the gasoline fraction ($C_5^+$), as the reaction temperature rises, we see an increase in aromatic hydrocarbons (benzene, toluene), with the production of xylenes displaying a maximum yield at 560° C., as demonstrated by the data on overall yield presented in Table 5. As well as offering high economic value for the petrochemical industry, these aromatic hydrocarbons also contribute to improvement of the number of octanes in a gasoline (C5+) formulation.

TABLE 5

| Yield, wt. % | TRX, ° C. | | | | |
|---|---|---|---|---|---|
| | 520 A | 550 B | 580 C | 600 D | 620 E |
| Benzene | 0.21 | 0.32 | 0.52 | 0.73 | 1.02 |
| Toluene | 0.94 | 1.30 | 1.95 | 2.38 | 3.23 |
| Xylenes | 1.22 | 1.51 | 1.95 | 0.56 | 0.72 |

In the following, to demonstrate the gains of the process more clearly, Table 6 shows the comparative yields, by weight, between the processing of a reference stream of hydrofined diesel and the processing of a stream of refined soya oil directly in the FCC process. It also shows the yield in the processing of refined soya oil in the combined Hydroconversion/FCC process. The tests in the FCC pilot-plant unit were carried out at a temperature of 600° C. with three different feeds, namely:

D1=hydrofined diesel oil—HDT.

D2=refined soya oil without undergoing the hydroconversion stage—HDT.

D3=liquid fraction after separation of the products formed in the hydroconversion stage—HDT of the feed of refined soya oil.

TABLE 6

| Yield, wt. % | D1 | D2 | D3 | Δ (D3 − D2) |
|---|---|---|---|---|
| Fuel Gas | 6.5 | 5.8 | 4.6 | −1.2 |
| $C_2^=$ | 9.7 | 11.5 | 11.9 | 0.32 |
| $C_3$ | 2.6 | 2.0 | 11.3 | 9.3 |
| $C_3^=$ | 17.1 | 18.2 | 22.6 | 4.4 |
| $C_4$ | 2.2 | 7.8 | 5.1 | −2.7 |
| $C_4^=$ | 7.7 | 1.5 | 11.9 | 10.4 |
| $C_5$ –221° C. | 30.1 | 27.4 | 18.0 | −9.4 |
| LCO, 221-343° C. | 14.8 | 5.8 | 1.5 | −4.3 |
| DO, 221-343° C. | 5.3 | 1.7 | 0 | −1.7 |
| Coke | 4.1 | 5.3 | 1.1 | −4.2 |
| Conversion | 75.8 | 87.2 | 97.4 | 10.2 |
| Oxygenated products ($H_2O$ + CO + $CO_2$) | 0 | 12.9 | 13.6 | 0.7 |
| Conversion (*) | 75.8 | 74.3 | 83.8 | 9.5 |

According to Table 6, there is a significant increase in the yield of olefins in the process that combines hydroconversion and catalytic cracking (D3), when compared with the catalytic cracking of refined soya oil (D2) and with the hydroconversion and of diesel oil from hydrofined petroleum (D1), used as reference. Advantageously, the degree of conversion becomes more evident when the conversion (*) in the catalytic cracking of soya oil is calculated by subtraction of the conversion of the oxygenated products. It can be seen that the value is similar when D1 and D2 are processed, however the value is far higher for the process D3 of the invention, which combines hydroconversion and fluid catalytic cracking.

For further confirmation of the gains with the greater process severity, Table 7 below presents the results with the comparative data of the FCC stage, at a temperature of 620° C., with the three different feeds, D1, D2 and D3, showing the even more significant gains in ethylene ($C_2^=$) and propylene ($C_3^=$) with a 20° C. increase in the temperature, compared with the data in Table 6. Advantageously, there is even greater conversion (*) with significant reduction in the yield of coke, DO, LCO and fuel gas. This result confirms that the process minimizes the formation of undesirable products, for this process severity, maximizing the production of light olefins ($C_2^=$ and $C_3^=$)

TABLE 7

| Yield, wt. % | D1 | D2 | D3 | Δ (D3 − D2) |
|---|---|---|---|---|
| Fuel Gas | 10.3 | 7.8 | 5.8 | −2.0 |
| $C_2^=$ | 11.3 | 12.1 | 13.5 | 1.4 |
| $C_3$ | 3.3 | 1.9 | 11.2 | 9.3 |
| $C_3^=$ | 15.7 | 16.7 | 23.3 | 6.6 |
| $C_4$ | 6.3 | 6.5 | 4.5 | −2.0 |
| $C_4^=$ | 1.9 | 1.2 | 10.5 | 9.3 |
| $C_5$ –221° C. | 28.6 | 27.1 | 16.3 | −10.9 |
| LCO, 221-343° C. | 11.5 | 5.5 | 1.3 | −4.2 |
| DO, 343° C. | 4.9 | 1.9 | 0.1 | −1.8 |
| Coke | 6.2 | 6.2 | 1.7 | −4.5 |
| Conversion | 77.4 | 86.4 | 96.9 | 10.5 |
| Oxygenated products ($H_2O$ + CO + $CO_2$) | 0 | 13.1 | 13.6 | 0.5 |
| Conversion (*) | 77.4 | 73.3 | 83.4 | 10.1 |

Therefore the process described, with examples, combines hydroconversion and catalytic cracking of a feed containing triglycerides from vegetable and/or animal biomass and provides high yields of light olefins, chiefly ethylene ($C_2^=$) and propylene ($C_3^=$), which are of considerable economic importance for the petrochemical industry, with a degree of conversion greater than 80%.

The invention claimed is:

1. Process for production of light olefins from a feed containing triglycerides, characterized in that it maximizes the production of ethylene and propylene comprising the following steps:
   a) hydroconversion of a feed containing triglycerides with fatty acids of C9-C18 carbon chain, in contact with a hydrogen-rich gas stream, on a catalyst of metal oxides to produce: a fraction of fuel gas and water vapour; a gaseous fraction constituted principally of propane; and a liquid fraction of saturated hydrocarbons and dissolved gases;
   b) separation of the liquid fraction of saturated hydrocarbons comprising predominantly C9-C18 linear carbon chains; and
   c) fluid catalytic cracking of the separated liquid fraction, in petrochemical conditions, with a catalyst bed constituted predominantly of zeolites, in proportions between 30 and 70 wt. %, temperature at reactor outlet between 450° C. and 620° C., residence time between 1 and 10 seconds inside the reactor and with injection of steam between 5 and 50 wt. % relative to the feed entering the reactor.

2. Process according to claim 1, characterized in that the feed contains triglycerides with fatty acids of (C9-C18) carbon chain obtained from vegetable and/or animal biomass.

3. Process according to claim 1, characterized in that the feed contains triglycerides with concentrations of fatty acids above 65 wt. %.

4. Process according to claim 1, characterized in that the feed is selected from soya oil (*Glycine max*), castor oil (*Ricinus communis*), cottonseed oil (*Gossypium hirsutum* or *G. barbadenseis*), oil of Brazilian oil palm (*Elaies guinensis*), pine oil (tall oil), sunflower oil (*Helianthus annuus*), oil of Barbados nut or Physic nut (*Jatropha curcas*), seaweed oil, tallow and other oils of animal or vegetable origin.

5. Process according to claim 1, characterized in that the feed comprises a single oil or a mixture of two or more oils, in any proportions.

6. Process according to claim 1, characterized in that the triglycerides are fully hydrogenated in the hydroconversion step, in conditions of temperature between 280° C. and 370° C., hydrogen partial pressure between 1 MPa and 10 MPa and space velocity LHSV between 0.5 and 2.5 h−1, defined in accordance with the molecular structure of the triglycerides in the feed, on a catalyst bed of sulphided metal oxides supported on gamma alumina, MgO or silica/alumina.

7. Process according to claim 2, characterized in that the metal oxides are selected from the pairs Ni and Mo, Co and Mo, or Ni and W.

8. Process according to claim 1, characterized in that the liquid fraction of saturated hydrocarbons is produced in the hydroconversion step at yield above 80%.

9. Process according to claim 1, characterized in that the liquid fraction is constituted predominantly of saturated linear (C9-C18) hydrocarbons.

10. Process according to claim 1, characterized in that the catalyst contains zeolite that is selective for light olefins with silica-alumina ratio equal to 10 or more.

11. Process according to claim 10, characterized in that the element phosphorus is incorporated in the catalyst by treatment of the zeolites.

12. Process according to claim 10, characterized in that the catalyst contains zeolite that is selective for light olefins in proportions between 1 and 55 wt. % relative to the total zeolites in the catalyst.

13. Process according to claim 1, characterized in that the LCO produced in the catalytic cracking step is recycled to the reactor to increase the production of light olefins.

14. Process according to claim 1, characterized in that the propane fraction generated in the hydroconversion step is incorporated in the stream of propane produced in the process.

15. The process according to claim 10, characterized in that the catalyst contains zeolite that is ZSM-8, ZSM-11 or ZSM-12.

16. The process according to claim 10, characterized in that the catalyst contains zeolite that is ZSM-5 (MFI).

17. The process according to claim 1, characterized in that the production of light olefins has a degree of conversion greater than 80 wt. %.

18. The process according to claim 17, characterized in that the production of light olefins has a degree of conversion greater than 90 wt.%.

* * * * *